United States Patent [19]

Burgin et al.

[11] Patent Number: 4,969,869
[45] Date of Patent: Nov. 13, 1990

[54] PILLOW CONSTRUCTION AND MEDICATION DISPENSER

[76] Inventors: Kermit H. Burgin, R.R. #1, Box 334, Whitestown, Ind. 46075; George R. Newman, 2330 Sykes Creek Pkwy., Merritt Island, Fla. 32952

[21] Appl. No.: 295,576

[22] Filed: Jan. 11, 1989

Related U.S. Application Data

[63] Continuation of Ser. No. 71,989, Jul. 9, 1987, Pat. No. 4,826,479.

[51] Int. Cl.$^5$ ............................................. A61M 37/00
[52] U.S. Cl. ..................................... 604/23; 604/289
[58] Field of Search ..................... 604/289, 23; 35/279; 128/155 (U.S. only), 156

[56] References Cited

U.S. PATENT DOCUMENTS

| | | |
|---|---|---|
| 233,954 | 11/1880 | Thompson . |
| 290,608 | 12/1883 | Snyder . |
| 618,210 | 1/1899 | Shakespeare . |
| 1,777,982 | 10/1930 | Popp . |
| 1,876,591 | 9/1932 | Bawden . |
| 2,162,999 | 6/1939 | Frank . |
| 2,305,173 | 12/1942 | Leeb ..................................... 604/23 |
| 2,500,974 | 3/1950 | Angert . |
| 2,858,830 | 11/1958 | Robins . |
| 2,917,046 | 12/1959 | Fairbanks . |
| 3,266,064 | 8/1966 | Figman . |
| 3,610,238 | 10/1971 | Rich, Jr. ................................. 604/23 |
| 4,277,859 | 7/1981 | Seaman . |
| 4,604,114 | 8/1986 | Ward ..................................... 55/279 |
| 4,607,403 | 8/1986 | Alivizatos . |
| 4,646,731 | 3/1987 | Brower . |
| 4,807,613 | 2/1989 | Koehnke et al. .................... 128/155 |

FOREIGN PATENT DOCUMENTS

| | | |
|---|---|---|
| 473604 | of 1929 | Fed. Rep. of Germany . |
| 2226444 | 5/1972 | Fed. Rep. of Germany ........ 604/23 |
| 780514 | of 1835 | France . |

*Primary Examiner*—Randall L. Green
*Assistant Examiner*—K. M. Reichle
*Attorney, Agent, or Firm*—Barnes & Thornburg

[57] ABSTRACT

A pad for use with a gas permeable pillow, mattress, or the like having a stream of gas or mixture of gases flowing outwardly from the pillow, mattress or the like, the pad comprising a material which is substantially permeable to the gas or mixture of gases, the material being impregnated by a treating composition capable of being carried by the gas or mixture of gases to dispense the treating composition to expose a person or animal resting on the pillow, mattress, or the like to the treating composition and the pad being mounted on the pillow, mattress, or the like in the stream of gas or mixture of gases.

7 Claims, 1 Drawing Sheet

PILLOW CONSTRUCTION AND MEDICATION DISPENSER

This is a continuation of application Ser. No. 07/071,989 filed July 9, 1987, now U.S. Pat. No. 4,826,479.

This invention relates to pillow constructions and particularly to a pillow construction which can be achieved economically and which permits a medication-dispensing capability to be incorporated into the pillow.

It is an object of the invention to provide an economical pillow construction.

It is a further object of the invention to provide a medication-dispensing structure which can be used in conjuction with the simple pillow construction, with a modified pillow construction, or with some other item of bedding or the like.

It is a further object of the present invention to provide a modified pillow construction which enhances the transport of medication, either from a medication-dispensing structure used in conjunction therewith, or from a separate source of a medication, to the person or animal resting on the pillow.

According to one aspect of the invention, a pillow comprises an inner substantially impermeable layer forming a pocket, means for introducing a substance to which the inner layer is substantially impermeable through the substantially impermeable layer into the pocket to inflate the pillow, and a covering layer comprising a woven or non-woven textile-like material.

Illustratively, the covering layer substantially covers both sides of the pillow.

According to this aspect of the invention, the pillow further comprises a means defining an additional field interposed between the substantially impermeable layer and the covering layer, and means for providing access to the additional field to permit introduction into the additional field of a gas or mixture of gases for carrying a treating composition. The covering layer is substantially permeable to the treating composition entrained in the carrier gas or mixture.

Additionally, according to this aspect of the invention, the means defining the additional field comprises lengths of resilient tubing, each having a first and a second end, a manifold having means defining an entry port for providing access to the additional field, and means for coupling the first ends of the lengths of tubing to the manifold in open communication to receive the gas or mixture of gases. Each length of tubing includes means defining an opening through its sidewall along its length to permit the escape of the gas or mixture of gases introduced into the manifold from the lengths of tubing.

Further according to this aspect of the invention, the pillow further comprises means defining an additional field interposed between the substantially impermeable layer and the covering layer, and means for providing access to the additional field to permit introduction into the additional field of a gas or mixture of gases, the covering layer being substantially permeable to the carrier gas or mixture. A pad substantially permeable to the gas or mixture of gases and impregnated by a treating composition capable of being carried by the gas or mixture of gases is included. Means are provided for affixing the pad to the covering layer over the additional field.

In addition, according to this aspect of the invention, the means for affixing the pad to the covering layer comprises an adhesive on a surface of the pad.

Illustratively, the pad further comprises a protective strip for covering the adhesive. Removal of the protective strip activates the adhesive to permit the pad to be affixed to the covering layer.

According to another aspect of the invention, a pad is constructed from a material which is substantially permeable to a gas or mixture of gases. The pad is impregnated by a treating composition capable of being carried by the gas or mixture of gases, and means are provided for mounting the pad in a stream of the gas or mixture of gases.

According to this aspect of the invention, the means for mounting the pad in a stream of the gas or mixture of gases comprises an adhesive on a surface of the pad for adhering the pad to a substrate.

Further according to this aspect of the invention, a protective strip is provided for covering the adhesive. Removal of the protective strip activates the adhesive to permit the pad to be affixed to the substrate.

The invention may best be understood by referring to the following description and accompanying drawings which illustrate the invention. In the drawings.

Figure 1:
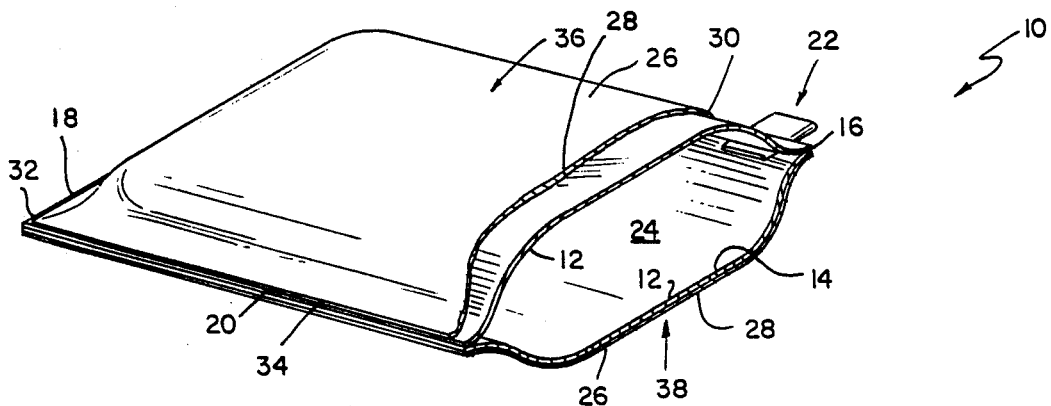
FIG. 1 illustrates a partly fragmentary perspective view of an economical pillow construction according to the present invention.

Referring now to FIG. 1, the construction of an econmical pillow or cushion 10 includes an inner layer 12 of a substantially gas- or other filler-impermeable material sheet such as a resin or so-called plastic material sheet. The inner layer 12 is constructed illustratively from a single sheet 14 doubled over and joined, for example, by heat welding or by a suitable adhesive, along its edges 16, 18, 20. Alternatively two sheets can be joined, for example, by heat welding or suitable adhesive, along their contiguous edges. A port 22 is provided through the joined edges at a suitable location along the perimeter, at edge 16 for the introduction into the interior 24 thus formed, and the removal from the interior 24, of some material such as air or shredded paper, with which the pillow 10 is inflated or stuffed to a desired size.

The impermeable portion 12 of the pillow 10 is covered by a permeable textile or textile-like woven paper sheet or a sheet of paper 26 otherwise treated to render it soft to the touch so that it does not irritate the skin, for example, of a user. As with the resin 12, the textile or paper 26 can be in the form of a single sheet 28 folded over and joined to the edges 16, 18, 20 of sheet 14 by suitable adhesives along its free edges 30, 32, 34, respectively. Alternatively, two sheets of similar or dissimilar materials can be joined along their edges to the edges of the impermeable portion 12 to cover it on both sides. If the same or similar materials are used, of course, the two sides 36, 38 of the resulting pillow 10 will be the same or similar. If dissimilar materials are used, then the two sides 36, 38 of the pillow 10 will be correspondingly dissimilar. Alternatively, the permeable textile or paper sheet 26 can be provided on one side, for example, side 36, only, with the intention being that that is the side on which the user will rest.

Figure 2:
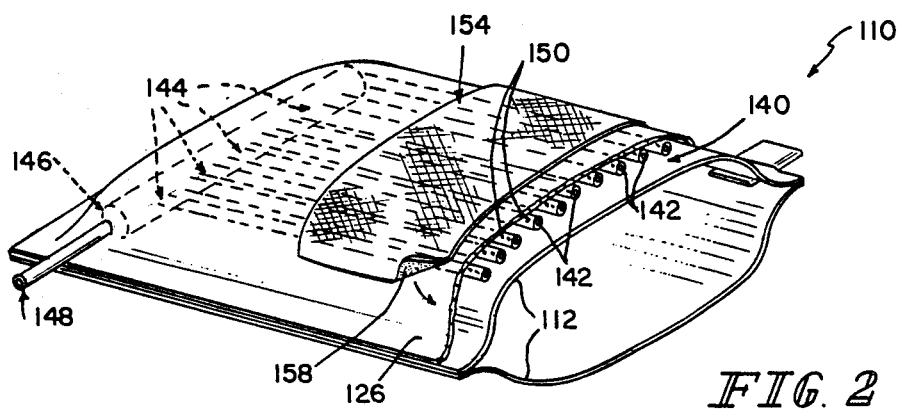
FIG. 2 illustrates a partly fragmentary perspective view of a modified pillow construction according to the present invention, with a medication-dispensing structure according to another aspect of the present invention attached thereto.

In the embodiment of the invention illustrated in FIG. 2, a tube field 140 is added between the impermeable 112 and textile or paper 126 sheets. The illustrated tube field 140 is in the form of a number of tubes 142 which extend generally parallel lengthwise of the pillow 110. An illustrative material for the tubes 142 is that sold under trademark "TYGON". Each of the tubes 142 is joined at one 144 of its ends to a manifold 146 which is common to the tubes 142. An inlet 148 to the manifold permits a gas or mixture of gases, for example, air, bearing a medicament, such as camphor, a water fog, a pesticide such as flea medicine, or the like, to be pumped into the field 140. Each tube 142 is provided with openings 150 in the sidewall thereof along its length opening in a common direction outward away from layer 112. Since the textile or paper layer 126 is permeable by this gas/entrained medicament, the person or animal resting on the pillow 110 is exposed to the medicament for treatment by it.

Figure 3:
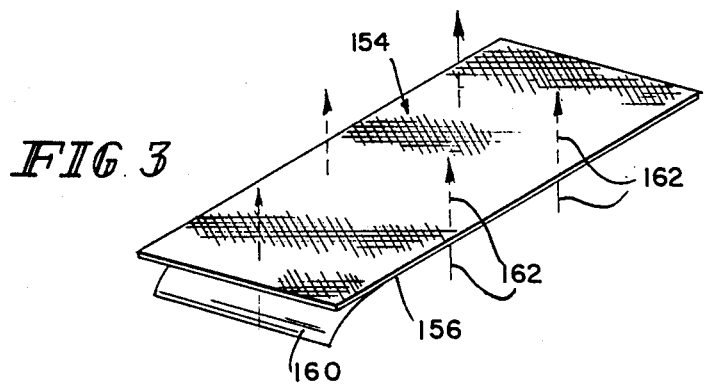
FIG. 3 illustrates a perspective view of the medication-dispensing structure by itself.

As an alternative to suspension of the medicament in the carrier gas which is pumped through the tube field 140, the carrier gas without the medicament disposed in it can be pumped through the tube field 140. A medicament bearing pad 154, one side 156 of which is illustratively provided with an adhesive 158, can then be applied to the gas/entrained medicament permeable layer 126 over the tube field 140. The release of air or other carrier gas from the tube field 140 through the gas/entrained medicament permeable layer 126 and the pad 154 entrains the medicament from the medicament-bearing pad 154 and bears the medicament to the person or animal to whom or to which it is to be applied. The pad 154 illustratively is a gauze, gauze-like or textile-like pad impregnated with the medicament. The adhesive 158 may be a pressure sensitive type such as is normally found on bandages and adhesive tape and may be covered with a protective strip 160 which keeps the pad 154 from adhering to a surface except when the protective strip 160 is removed. The construction of the pad 154 itself and arrows 162 illustrating airflow through it are illustrated in FIG. 3.

Figure 4:
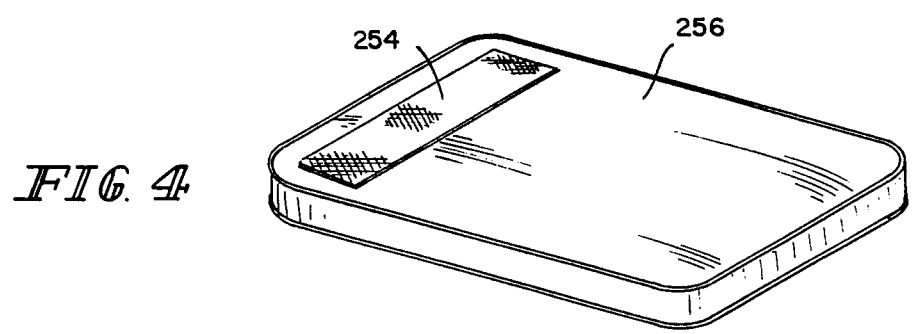
FIG. 4 illustrates a perspective view of the medication-dispensing structure attached to the top surface of a mattress.

In certain cirumstances, the medicament with which the pad is impreganted may be sufficiently volatile, or the desired evaporation rate of the medicament from the pad sufficiently slow that natural circulation through the pad itself, without the aid of gas circulated through a field, may be sufficient to dispense the medicament. This may particularly be the case where, as illustrated in FIG. 4, the pad 254 can be applied to a mattress 256, such as the mattress of a baby crib, and the movement of the person or animal on the mattress 256 "pumps" air through the mattress 256 and the pad 254 applied thereto.

What is claimed is:

1. A pad for use with a gas permeable pillow, mattress, or the like, the pad being constructed from a material which is substantially permeable to a gas or mixture of gases, the pad impregnated by a treating composition capable of being carried by the gas or mixture of gases, and means for mounting the pad on the pillow, mattress, or the like in a stream of the gas or mixture of gases.

2. The pad of claim 1 wherein the means for mounting the pad in a stream of the gas or mixture of gases comprises an adhesive on a surface of the pad for adhering the pad to the pillow, mattress, or the like.

3. The pad of claim 2 and further comprising a protective strip for covering the adhesive, removal of the protective strip activating the adhesive to permit the pad to be affixed to the pillow, mattress, or the like.

4. A pad for use with a gas permeable pillow, mattress, or the like having a stream of gas or mixture of gases flowing outwardly from the pillow, mattress, or the like, the pad comprising a material which is substantially permeable to the gas or mixture of gases, the material being impregnated by a treating composition capable of being carried by the gas or mixture of gases to dispense the treating composition to expose a person or animal resting on the pillow, mattress, or the like to the treating composition, and means for mounting the pad on the pillow, mattress, or the like in the stream of gas or mixture of gases.

5. The pad of claim 4 wherein the treating composition comprises a volatile medicament so that movement of the person or animal on the pillow, mattress, or the like generates air movement through an external surface of the pillow, mattress, or the like which is sufficient to dispense the medicament from the pad.

6. The pad of claim 4 wherein the means for mounting the pad on the pillow, mattress, or the like comprises an adhesive on the surface of the pad for adhering the pad to an external surface of the pillow, mattress, or the like.

7. The pad of claim 6 and further comprising a protective strip for covering the adhesive, removal of the protective strip activating the adhesive to permit the pad to be affixed to the external surface of the pillow, mattress, or the like.

* * * * *